Figure 2A:
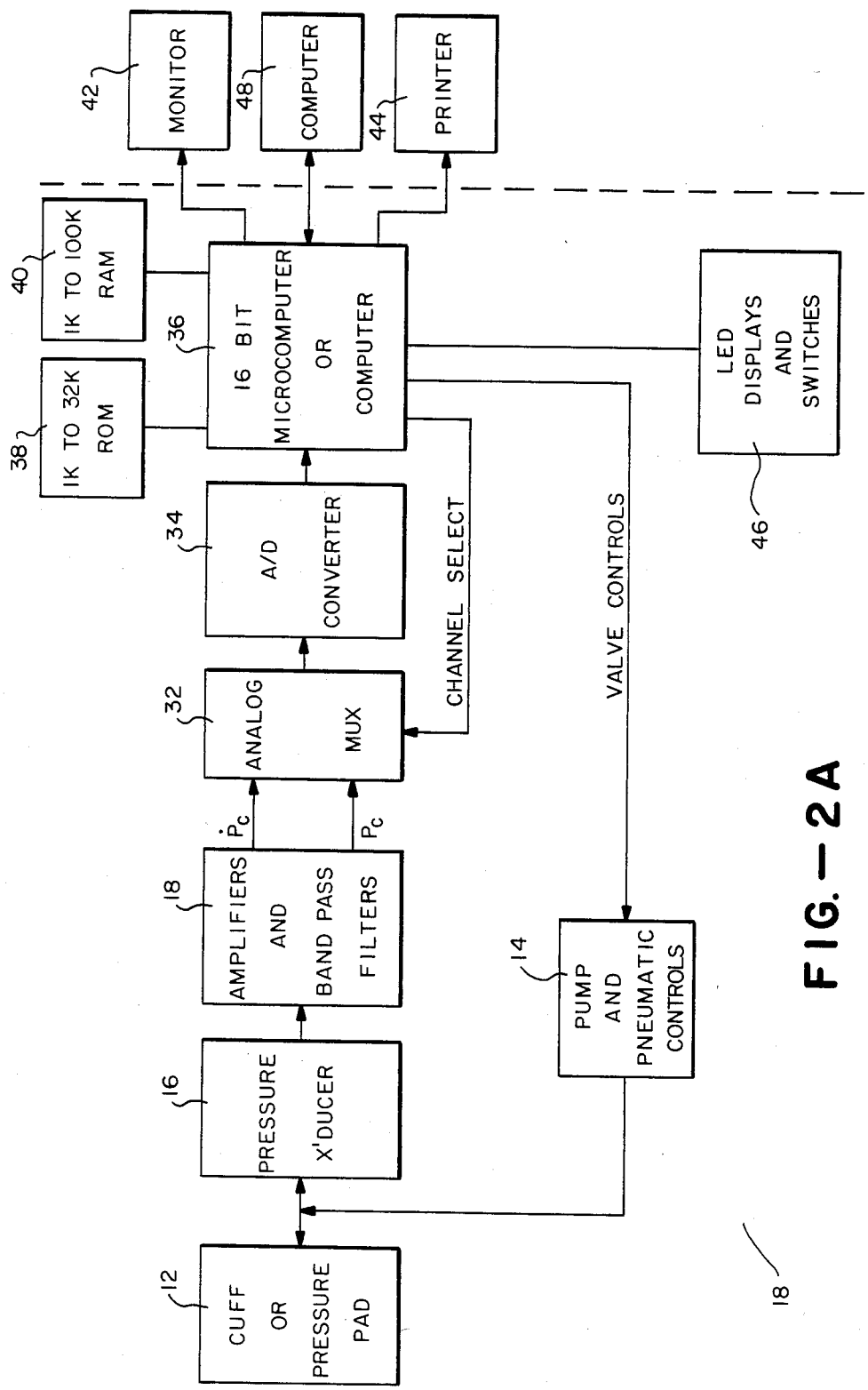

United States Patent [19]

Link

[11] Patent Number: 4,712,563
[45] Date of Patent: Dec. 15, 1987

[54] METHOD OF AND APPARATUS FOR DETERMINING THE DIASTOLIC AND SYSTOLIC BLOOD PRESSURE OF A PATIENT

[75] Inventor: William T. Link, Berkeley, Calif.

[73] Assignee: Baxter Travenol Laboratories, Inc., Deerfield, Ill.

[21] Appl. No.: 868,400

[22] Filed: May 28, 1986

[51] Int. Cl.⁴ ............................................. A61B 5/02
[52] U.S. Cl. .................................................. 128/681
[58] Field of Search ............................... 128/680–683; 364/417

[56] References Cited

U.S. PATENT DOCUMENTS

| | | | |
|---|---|---|---|
| 3,903,872 | 9/1975 | Link | 128/681 |
| 4,105,021 | 8/1978 | Williams et al. | 128/683 |
| 4,177,801 | 12/1979 | Grangirard et al. | 128/681 |
| 4,271,843 | 6/1981 | Flynn | 128/681 |
| 4,360,029 | 11/1982 | Ramsey, III | 128/681 |
| 4,427,013 | 1/1984 | Numa et al. | 128/681 |
| 4,461,266 | 7/1984 | Hood, Jr. et al. | 128/681 |
| 4,464,123 | 8/1984 | Glover et al. | 128/681 X |
| 4,546,775 | 10/1985 | Medero | 128/680 X |
| 4,592,365 | 6/1986 | Georgi | 128/680 |

Primary Examiner—Kyle L. Howell
Assistant Examiner—Francis J. Jaworski
Attorney, Agent, or Firm—Flehr, Hohbach, Test, Albritton & Herbert

[57] ABSTRACT

A technique is disclosed herein for obtaining the diastolic and systolic blood pressures of a particular patient by generating cuff pulses of the patient and using these cuff pulses as the only information relating to the blood pressure of the patient in order to determine the diastolic and systolic pressures.

4 Claims, 6 Drawing Figures

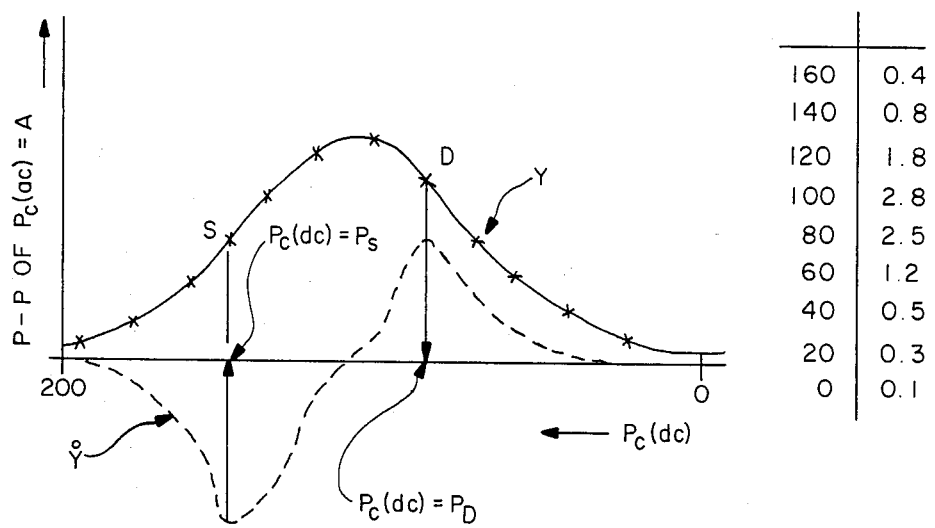
FIG.—1
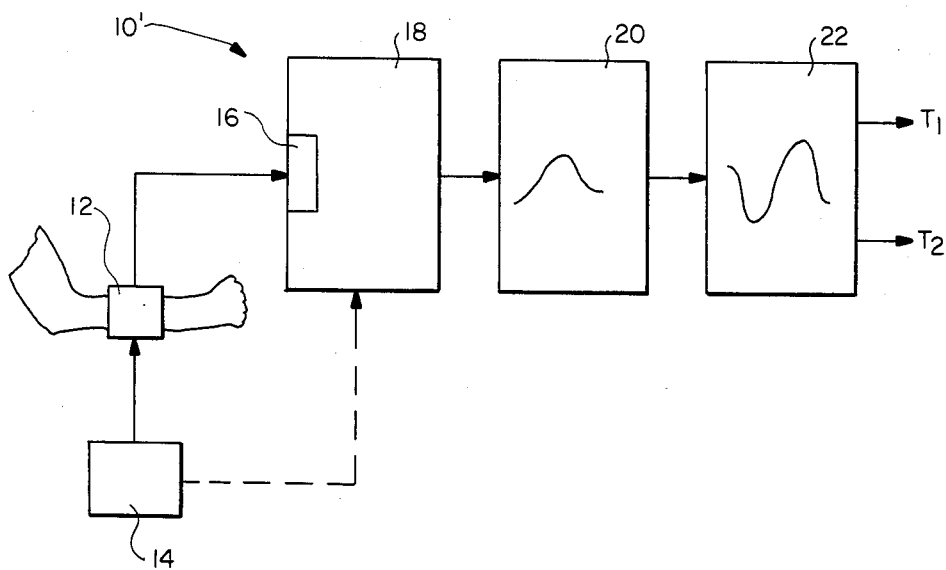
FIG.—2

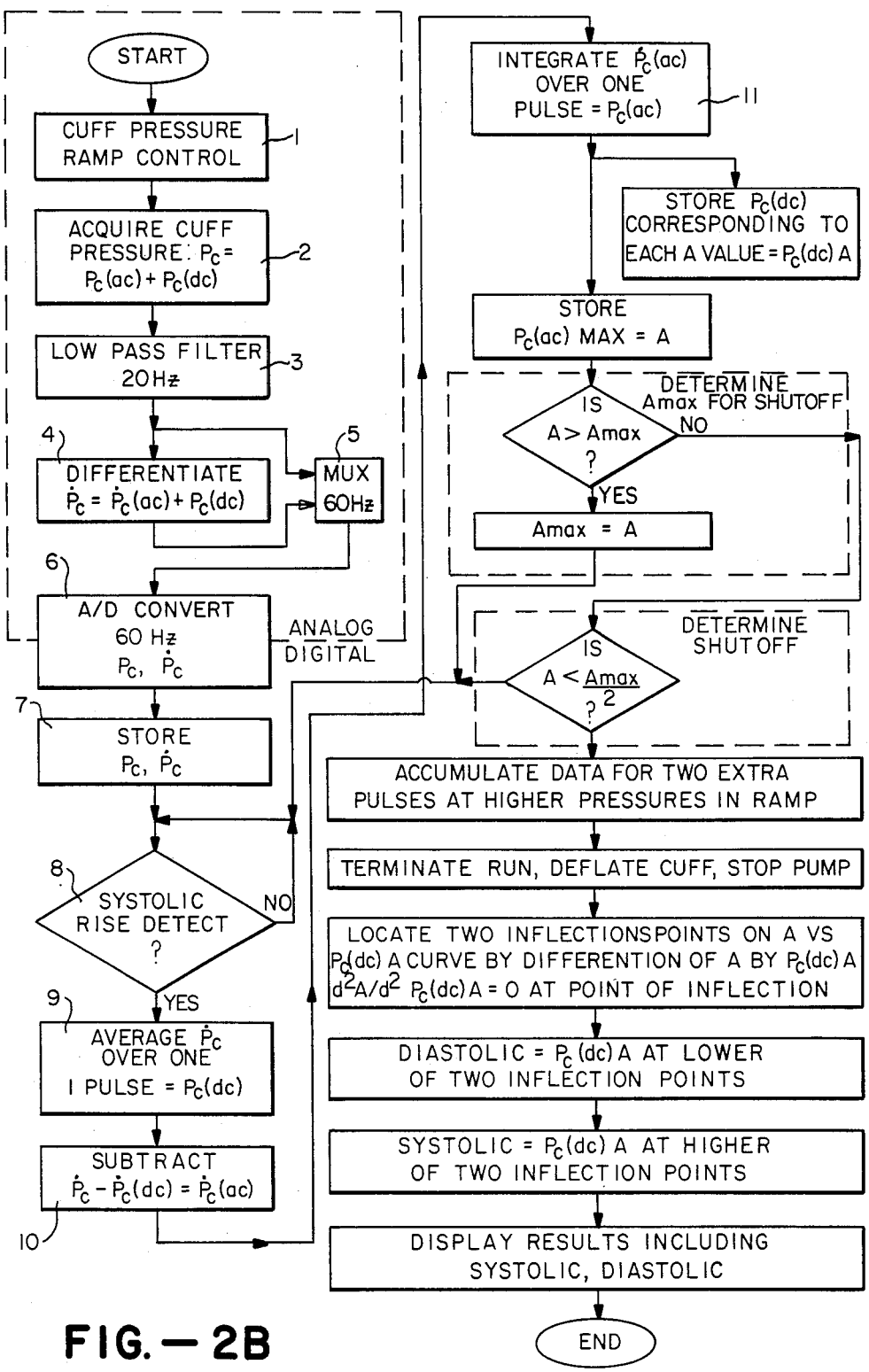
FIG.—2B

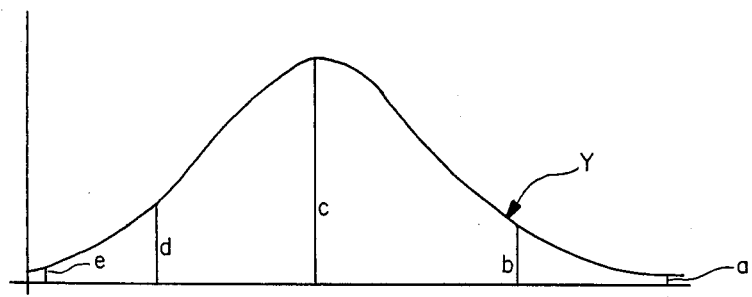
FIG.—3
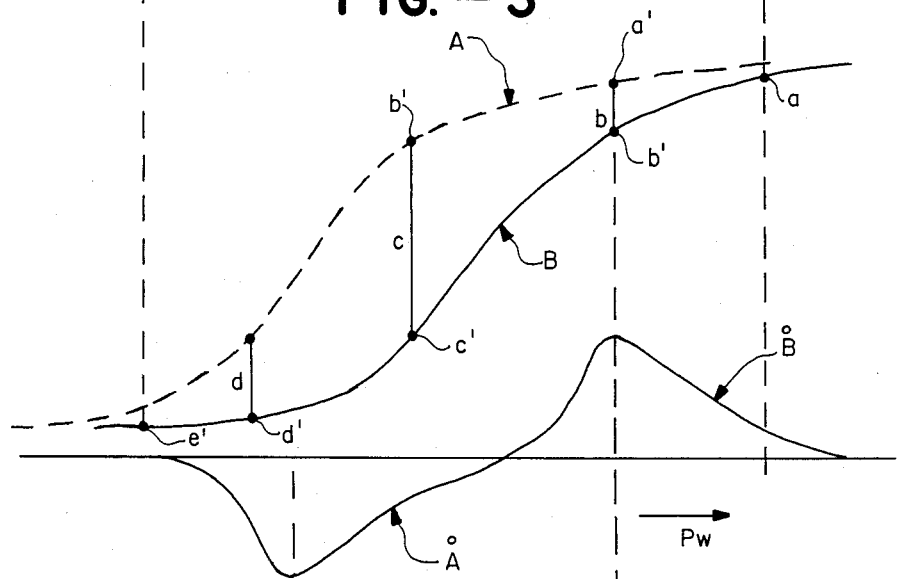
FIG.—4
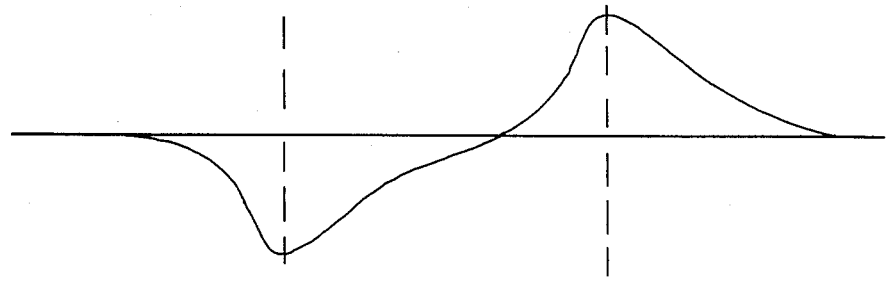
FIG.—5

METHOD OF AND APPARATUS FOR DETERMINING THE DIASTOLIC AND SYSTOLIC BLOOD PRESSURE OF A PATIENT

The present invention relates generally to blood pressure evaluation procedures and more particularly to a specific technique for obtaining the diastolic and systolic pressures of a patient by means of oscillometry.

A number of techniques for obtaining different information about a patient's blood pressure oscillometrically are disclosed in applicants' copending U.S. application Ser. Nos.: 622,213 (filed June 19, 1984); 622,073, (filed June 19, 1984); 622,080 (filed June 19, 1984); and 622,079, (filed June 19, 1984), all of which are incorporated herein by reference. In addition, applicant's own U.S. Pat. No. 3,903,872 (the Link patent) describes a specific technique for obtaining the diastolic blood pressure of a patient while U.S. Pat. Nos. 4,009,709 and 4,074,711 (Link et al) describe specific techniques for obtaining a patient's systolic pressure. These patents are also incorporated herein by reference.

It is an object of the present invention to provide still another technique for obtaining the diastolic and systolic blood pressures of a patient by means of oscillometry.

It is a more particular object of the present invention to provide an extremely uncomplicated oscillometric technique for obtaining a patient's diastolic and systolic blood pressures.

As described in the Link and Link et al patents and the pending LINK applications recited above, oscillometric cuff pulses of a patient can be generated by positioning a blood pressure cuff, pad or other suitable means (hereinafter merely referred to as a cuff) against a cooperating artery of the patient and thereafter pressurizing the cuff to different levels, typically from no pressure at all to pressures exceeding the anticipated systolic pressure of the patient. At any given cuff pressure level, the pressure within the cuff continuously changes in an oscillating fashion due to the combination of (1) the internal pressure changes in the patient's artery and (2) the particular pressure level in the cuff. These oscillating changes in pressure are referred to as cuff pulses and vary in size and shape with changes in cuff pressure. The Link and Link et al patents and at least some of the pending Link applications utilize these cuff pulses as starting points to obtain the desired information about the patient's blood pressure. However, in accordance with the present invention, these cuff pulses are utilized as the only information relating to the blood pressure of the patient to obtain the patients diastolic and systolic blood pressure.

As will be discussed in more detail hereinafter, in order to determine a patient's diastolic and/or systolic blood pressures, cuff pulses of the patient are generated at cuff pressure levels from a level below the anticipated diastolic pressure of the patient to a pressure above the patient's anticipated systolic pressure so as to obtain peak to peak amplitude values corresponding to and dependent on the different cuff pressure levels. The patients diastolic and systolic pressures are obtained mathematically by generating a curve corresponding to these peak to peak amplitude values as a function of the different cuff pressure levels. This curve is then mathematically differentiated with respect to the different cuff levels. The differentiated curve includes a first peak point which applicant has discovered corresponds to a cuff pressure level equal to the diastolic pressure of the patient and a second peak point which applicant has also discovered corresponds to a cuff pressure level equal to the systolic pressure of the patient. Therefore, it is only necessary to identify these peak points and their respective cuff pressure levels in order to obtain the patient's diastolic and systolic pressures.

The technique just recited briefly will be described in more detail in conjunction with the drawings wherein:

FIG. 1 graphically illustrates the technique of obtaining a patient's diastolic and systolic pressures in accordance with the present invention;

FIGS. 2, 2A and 2B diagrammatically illustrate by means of a general block diagram, a more detailed block diagram and a flow diagram of an apparatus for carrying out the technique of FIG. 1; and FIGS. 3–5 graphically illustrate the validity of the technique of FIG. 1.

Turning now to the drawings, attention is immediately directed to FIG. 1 which graphically illustrates the peak to peak amplitude (P-P) of a particular patient's cuff pulses $Pc(ac)$ as a function of cuff pressure $Pc(dc)$, that is, the pressure levels of a cuff positioned around a cooperating artery of a patient. In the particular case illustrated, the cuff was pressurized from no pressure to 160 Torr. These pressure levels and the resultant peak to peak amplitudes resulting from these pressure levels are set forth in FIG. 1 along with a corresponding curve generally indicated by the letter Y. Note that the cuff pressure $Pc(dc)$ reads from right to left on the horizontal axis while the peak to peak amplitude P-P of the cuff pulses $Pc(ac)$ read upward on the vertical axis. The particular configuration of exemplary cuff pulses are illustrated in the pending Link applications and therefore will not be shown here. The peak to peak values of these cuff pulses can be readily obtained by those with ordinary skill in the art either visually or electronically, as will be discussed below in conjunction with FIG. 2. For the moment, it suffices merely to illustrate the numerical values and the resultant curve Y. In this regard, it is to be understood that these numerical values and the curve itself are being provided for illustrative purposes only and are not intended to limit the present invention.

In accordance with the present invention, curve Y is mathematically differentiated with respect to the different cuff pressure levels. This curve $dy/dPc(dc)$ is illustrated by dotted lines in FIG. 1 curve, which for brevity sake will be referred to as $\dot{Y}$. Note specifically that this curve includes two distinct peak values, a maximum peak value and a minimum peak value. Applicant has discovered that the maximum peak value coincides with a cuff pressure $Pc(dc)$ which is equal to the diastolic pressure of the patient while the minimum peak value coincides with a cuff pressure which is equal to the patients' systolic pressure. Thus, as a result of this finding, in order to determine the diastolic and systolic pressures of a patient, it is only necessary to generate cuff pulses of the patient at cuff pressures ranging from below the anticipated diastolic pressure of the patient to above the patients' anticipated systolic blood pressure. This curve can be differentiated mathematically and the maximum and minimum peak levels and their associated cuff pressures determined in order to obtain the patients' systolic blood pressures.

FIG. 2 diagrammatically illustrates an apparatus 10 for carrying out the procedure just described. This apparatus includes a blood pressure cuff 12 as defined previously which is specifically shown disposed against an artery of a patient. Suitable means generally indicated at 14 is provided for pressurizing the cuff to different cuff pressures Pc(dc) from a level below the anticipated diastolic pressure of the patient to a level above the patient's anticipated systolic level. A suitable transducer 16 and cooperating circuitry 18 are interconnected with the cuff to provide the resultant cuff pulses. Additional circuitry 20 and 22 generate curve Y and differentiated $\dot{Y}$, respectively, and the circuitry 22 also includes circuitry for locating the maximum and minimum points of the differentiated curve and the corresponding cuff pressures. These cuff pressures may be read out at suitable terminals t1 and t2 as the diastolic and systolic pressures of the patient, respectively.

Having described apparatus 10 illustrated in FIG. 2, attention is now directed to FIG. 2A which illustrates the apparatus by means of a more detailed block diagram. As illustrated there, the apparatus includes the previously recited blood pressure cuff or cuff means 12. Means 14 in the form of a pump and suitable pneumatic controls are also illustrated and serve to pressurize the cuff to the previously recited different pressure levels. Pressure transducer 16 is shown coupling the cuff to a combination of amplifiers and band pass filters for producing cuff pulses at different cuff pressures.

An analog MUX and A/D converter and a sixteen-bit microcomputer or any other suitable computer means indicated generally at 32, 34 and 36, respectively, and connected in the manner illustrated in FIG. 2A cooperate to provide means for digitizing the analog cuff pressure, i.e., the cuff pressures Pc and the derivative of the cuff pressure $\dot{Pc}$ where $Pc=Pc(ac)+Pc(dc)$. The microcomputer or computer generally is controlled by a suitable program stored in ROM 38 in order to carry out the necessary steps of overall apparatus 10. This program may vary in length from for example 1K bytes to as much as 32K bytes depending upon accuracy and other factors. The digitized values of cuff pressures Pc are stored by computer 36 in a RAM 40. The computer can then act on information so stored to provide curve Y to differentiate the curve and to locate the inflection points corresponding to the diastolic and systolic pressures and these values can be readily read out, visually by for example monitor 42, or permanently, by means of, for example, printer 44 or by means of an LED display 46 or possibly another computer 48.

Turning now to FIG. 2B, there is shown a flow diagram corresponding to the procedure described previously with respect to FIG. 1 and incorporating the various steps carried out by the computer forming part of the block diagram illustrated in FIG. 2A. Before proceeding with a description of this flow diagram, it should be noted that the term "Pc" therein refers to the combination of cuff pressure Pc(dc) and cuff pulses Pc(ac) and that the $\dot{Pc}$ refers to the derivative of Pc and therefore the sum of the derivative of the cuff pressure Pc(dc) plus the derivative of the cuff pulses Pc(ac). It should be further noted that the derivative of the cuff pressure Pc(dc) corresponds to the ramp gradient characteristic resulting from the way in which the blood pressure cuff is pressurized. More specifically, as each cuff pulse Pc(ac) is generated at a given cuff pressure Pc(dc) it is done at continuously greater or lesser cuff pressures which form a continuously upwardly extending or downwardly extending ramp.

As will be seen below, the first eleven steps (boxes) in the flow diagram of FIG. 2B serve to receive physical cuff pressures from the cuff and these cuff pressures are converted to electrical analog signals and then digital signals and eventually the ramp component or gradient of the overall signal which is signal $\dot{Pc}$ is eliminated so as to provide the cuff pulses Pc(ac) by themselves on a horizontal axis rather than along a ramp gradient. At the same time, the overall signal Pc and the cuff pulses Pc(ac) are differentiated.

Referring now specifically to the flow diagram, step one begins after the start button is depressed and corresponds to pressurizing the cuff at different upwardly ramping or downwardly ramping cuff pressures Pc(dc). In step two the transducer forming part of the overall system receives the cuff pressures and converts them to analog signals which are filtered for 60 hz and noise (step three). These signals Pc are then differentiated by box four and Pc and the differentiated $\dot{Pc}$ are alternately fed to an analog/digital converter (box six) by means of the multiplexor corresponding to box five. Both Pc and $\dot{Pc}$ are stored in RAM as represented by box seven. As this is done, the system as represented by box eight continuously searches for the beginning of the cuff pulse by specifically looking for the beginning of its systolic rise. When that is found, $\dot{Pc}$ is averaged (integrated) over a full pulse and therefore corresponds to $\dot{Pc}(dc)$ or the ramp gradient. Finally, as indicated in box ten, $\dot{Pc}(dc)$ is subtracted from $\dot{Pc}$ leaving $\dot{Pc}(ac)$ which is the differential without the ramp gradient. Box 11 integrates $\dot{Pc}(ac)$ to provide the cuff pulses by themselves, that is, without the ramp gradient. These separated cuff pulses and both Pc and $\dot{Pc}$ are stored in RAM.

Having obtained pulses Pc(ac), described above, the amplitude A of each can be readily stored and the process can be terminated once the systolic pressure or the anticipated systolic pressure of the subject has been reached and surpassed. This can be accomplished by determining the systolic pressure by another method as indicated in the flow chart, for example the method described in U.S. Pat. Nos. 4,009,709 and 4,074,711. Thereafter, cuff pulses higher than the estimated systolic pressure are provided and their amplitudes stored and the process is then terminated, that is, no further information is obtained from the patient. However, the information so obtained is then utilized to create curve Y and differential curve $\dot{Y}$ and the two inflection points corresponding to the diastolic and systolic pressures determined and read out, as indicated in the flow diagram.

It is to be understood that the present invention is not limited to the utilization of a blood pressure cuff per se. Any suitable blood pressure pad means capable of cooperating with the patient to provide the patient's arterial pulses at any suitable artery including the temporal artery or branches thereof can be utilized. For purposes herein these various pressure applications will merely be referred to as cuff means and are not intended to be limited to a cuff specifically. Finally, the present invention is based on the assumption that the patient's cuff pulses that are generated are pure, that is, free of noise and that therefore, the curve Y is pure (free of noise). However, practically speaking, unless a patient whose cuff pulses are being taken holds his breath in a certain way and is completely still, the cuff pulses will include noise as a result of the patient breathing or moving. In order to provide an accurate reading of the patient's diastolic and systolic pressures in accordance with the present invention, these noises must be prevented from occurring, eliminated electronically or taken into account.

Having described a technique for determining the diastolic and systolic blood pressures of a patient in accordance with the present invention, attention is now directed to FIGS. 3-5 for a discussion of the validity of this technique. Referring first to FIG. 3, the curve Y is redrawn without differentiated curve $\dot{Y}$ and five specific peak to peak amplitudes have been selected and emphasized. For purposes of this discussion, they will be designated as having amplitude levels a, b, c, d and e. Also for purposes of this discussion, it will be assumed that the curve Y is that of a patient having known diastolic and systolic pressures and that the cuff pressure Pc(dc) corresponding to the peak to peak value a is zero. The cuff pressure corresponding to peak to peak amplitude b is greater than zero by an amount equal to the patient's pulse pressure $\Delta P$ which is the difference between the patient's systolic blood pressure $P_s$ and his diastolic pressure $P_d$. In a similar manner, the cuff pressure Pc(dc) corresponding to the peak to peak amplitude c is greater than the cuff pressure corresponding the peak to peak amplitude b by an amount equal to the patient's pulse pressure, and so on with respect to peak to peak amplitudes d and e. The reasons for selecting these cuff pressure values will become apparent hereinafter.

Attention is now directed to applicant's specific pending patent application Ser. No. 622,080 recited above. In this pending application, the peak to peak amplitudes of a patient's cuff pulses and the patient's diastolic and systolic pressures where utilized to generate an arterial (or transformation) curve for the patient. Such a curve is illustrated in FIG. 4 at B. Note that the curve B represents changes in arterial or cuff volume, actually cuff pressure Pc(ac), as a function of $P_{wall}$ ($P_w$) where $P_w$ equals the active blood pressure of the patient at any given time minus cuff pressure $P_c$(dc). This relationship is discussed in detail in both of the pending applications just recited. As described in these applications, a pressure band equal to the patient's pulse pressure ($P_s - P_d$) is used in conjunction with curve Y to establish the peak to peak amplitudes a, b, c, and so on in order to establish the corresponding points a' b' c' and so on for curve B. Thus, it is possible to generate this latter curve. The precise details of how this is done is left to the last-mentioned pending Link applications and reference is made thereto.

Once the patient's arterial or transformation curve B is generated, a second curve A is added to the same coordinate system. This curve A is actually curve B shifted to the left of curve B by an amount equal to the patient's pulse pressure $\Delta P$ ($P_s - P_d$). Thus, it should be apparent from FIG. 4 in conjunction with FIG. 3 that every point on curve A is located directly above a corresponding point on curve B by an amount equal to the peak to peak amplitude value on curve Y at the corresponding point. This is illustrated in FIG. 4 where the point a' on the B curve has been shifted to the left so that on the A curve it is located directly over a point b' on the B curve, the point b' on the B curve has been shifted to the left so that on the A curve it is located directly over the point c' on the B curve, and so on. From FIG. 4, is should be apparent that the point a' on the A curve is located an amount b above the point b' on the B curve, the point b' on the A curve is located an amount c above the point c' on the B curve, and so on. In other words, any given point on the A curve is directly above a corresponding point on the B curve by an amount equal to the peak to peak amplitude at the corresponding point on the Y curve. Stated another way, the Y curve is the difference between the A curve and the B curve or $Y = A - B$. An understanding and recognition of this relationship is critical to understanding the validity to the relationship between curve Y, its differential $\dot{Y}$ and the patient's diastolic and systolic pressures, as discussed above with respect to FIG. 1.

Still referring to FIG. 4, curves corresponding to the differential of curves of B and A as a function of $P_w$ are shown. While curves B and A were differentiated with respect to $P_w$ since $P_w$ equals $P_b - P_c$(dc) and since $P_b$ at any given point in time is a constant, the differential $dB/dP_w$ is equal to the differential $dB/dPc$(dc) and the differential $dA/dP_w$ is equal to $dA/dPc$(dc). Thus, it can be said that the two additional curves in FIG. 4 are $dB/dPc$(dc) and $dA/dPc$(dc) or, for brevity, $\dot{B}$ and $\dot{A}$. Since $Y = A - B$, $\dot{Y} = \dot{A} - \dot{B}$. Thus, taking into account arithmetic signs, it can be stated that the combination of $\dot{A}$ and $\dot{B}$ which is shown in FIG. 5 is equivalent to the differential of the curve Y. However, from the previously cited Link and Link et al patents and the Link pending applications, we know that $\dot{B}$ (the differential of arterial curve B) is the patient's compliance curve and the maximum point on that curve corresponds to the patient's diastolic pressure. Therefore, it can be concluded that the corresponding point on the differentiated curve $\dot{Y}$ corresponds to the patient's diastolic pressure.

From the discussion immediately above, it has been shown that by differentiating a patient's peak to peak curve Y, the patient's diastolic pressure can be obtained from one of the peaks of the differentiated curve. It will now be shown that the other peak is the patient's systolic pressure. To this end, it must be recalled that the curve A in FIG. 4 is actually curve B shifted to the left by one pulse pressure $\Delta P$. Therefore, any given point on curve B appears on curve A one pulse pressure to the left. As a result, the maximum slope of curve B (the peak of $\dot{B}$) is the same point on curve A but shifted to the left by one pulse pressure. Therefore, it can be said that the peak point on differentiated curve $\dot{A}$ is spaced to the left of the peak point of differentiated curve $\dot{B}$ by one pulse pressure. Therefore, since one pulse pressure is equivalent to the patient's systolic pressure minus his diastolic pressure and since the peak of curve $\dot{B}$ corresponds to the patient's diastolic pressure, the peak of curve $\dot{A}$ must correspond to the patient's systolic pressure. Thus, it has been shown that the second peak in the differentiated curve $\dot{Y}$ corresponds to the patient's systolic pressure.

The foregoing has been a description of a valid technique for obtaining the diastolic and systolic pressures of a patient by generating the patient's peak to peak curve from his cuff pulses and differentiating this latter curve. As stated above, this assumes that the peak to peak curve can be generated with negligible or no noise or that the noise can be compensated for. Also, even if a noise free peak to peak curve is generated, there is still a slight, negligible error between the peak values of the differentiated curve and the patient's diastolic and systolic pressures. This results from the fact that the sum of the curves $\dot{A}$ and $\dot{B}$ (see FIG. 4) causes a slight shift in their peak values relative to one another and therefore these peak values are not precisely in line with the peak values of the curve $\dot{Y}$. However, the difference is negligible and can be ignored or it can be readily compensated for mathematically (e.g., electronically).

What is claimed is:

1. A method of determining the diastolic and systolic blood pressures of a particular patient, comprising the steps of:
   (a) placing blood pressure cuff means adjacent a particular artery of said patient;
   (b) using means cooperating with said cuff means, pressurizing said cuff means to a number of different cuff pressure levels from a level below the anticipated diastolic pressure of the patient to a pressure above the patient's anticipated systolic pressure and generating cuff pulses having peak to peak amplitude values corresponding to and dependent on said different cuff pressure levels; and
   (c) electronically obtaining the diastolic and systolic pressures of said patient mathematically using said cuff pulses, said step of obtaining said diastolic and systolic pressures mathematically including the steps of:
      (i) generating a curve corresponding to the peak to peak amplitude values of said cuff pulses as a function of said different cuff pressure levels,
      (ii) differentiating said curve with respect to said different cuff pressure levels, said differentiated curve including a first peak point at a cuff pressure level equal to the diastolic pressure of said patient and a second peak point at a cuff pressure equal to the systolic pressure of said patient, and
      (iii) from said differentiated curve, obtaining the patient's diastolic and systolic pressures by identifying said first and second peak points and determining the cuff pressures at those points.

2. A method of determining the systolic blood pressure of a particular patient, comprising the steps of:
   (a) placing blood pressure cuff means adjacent a particular artery of said patient;
   (b) using means cooperating with said cuff means pressurizing said cuff means to a number of different cuff pressure levels form a level below the anticipated systolic pressure of the patient to a pressure above the patient's anticipated systolic pressure and generating cuff pulses having peak to peak amplitude values corresponding to and dependent on said different cuff pressure levels; and
   (c) electronically obtaining the systolic pressure of said patient mathematically using said cuff pulses, said step of obtaining said systolic pressure mathematically including the steps of:
      (i) generating a curve corresponding to the peak to peak amplitude values of said cuff pulses as a function of said different cuff pressure levels,
      (ii) differentiating said curve with respect to said different cuff pressure levels, said differentiated curve including a peak point at a cuff pressure level equal to the systolic pressure of said patient, and
      (iii) from said differentiated curve, obtaining the patient's systolic pressure by identifying said peak point and determining the cuff pressure levels at said point.

3. A method of determining the diastolic and systolic blood pressures of a particular patient, comprising the steps of:
   (a) placing blood pressure cuff means adjacent a particular artery of said patient;
   (b) using means cooperating with said cuff means, pressurizing said cuff means to a number of different cuff pressure levels form a level below the anticipated diastolic pressure of the patient to a pressure above the patient's anticipated systolic pressure and generating cuff pulses having peak to peak amplitude values corresponding to and dependent on said different cuff pressure levels; and
   (c) obtaining the diastolic and systolic pressures of said patient mathematically by
      (i) generating a curve corresponding to the peak to peak amplitude values of said cuff pulses as a function of said different cuff pressure levels,
      (ii) differentiating said curve with respect to said different cuff pressure levels, said differentiated curve including a first peak point at a cuff pressure level equal to the diastolic pressure of said patient and a second peak point at a cuff pressure equal to the systolic pressure of said patient, and
      (iii) from said differentiated curve, obtaining the patient's diastolic and systolic pressures by identifying said first and second peak points and determining the cuff pressure levels at said points.

4. An apparatus for determining the diastolic and systolic blood pressures of a particular patient, comprising:
   (a) blood pressure cuff means positionable adjacent a particular artery of said patient;
   (b) means cooperating with said cuff means for pressurizing said cuff means to a number of different cuff pressure levels form a level below the anticipated diastolic pressure of the patient to a pressure above the patient's anticipated systolic pressure;
   (c) means for generating cuff pulses having peak to peak amplitude values corresponding to and dependent on said different cuff pressure levels; and
   (d) means of obtaining the diastolic and systolic pressures of said patient mathematically using said cuff pulses, said means for obtaining said diastolic and systolic pressures mathematically including
      (i) means for generating a curve corresponding to the peak to peak amplitude values of said cuff pulses as a function of said different cuff pressure levels,
      (ii) means for differentiating said curve with respect to said different cuff pressure levels, said differentiated curve including a first peak point at a cuff pressure level equal to the diastolic pressure of said patient and a second peak point at a cuff pressure equal to the systolic pressure of said patient, and
      (iii) means responsive to said differentiated curve for obtaining the patient's diastolic and systolic pressure by identifying said first and second peak points and determining the cuff pressure levels at said points.

* * * * *